(12) United States Patent
Yaegashi et al.

(10) Patent No.: US 9,517,331 B2
(45) Date of Patent: Dec. 13, 2016

(54) IONTOPHORESIS PATCH

(75) Inventors: Mitsutoshi Yaegashi, Ashigarakami-gun (JP); Akihiro Hasui, Higashikagawa (JP); Hiroyuki Kubo, Chuo-ku (JP)

(73) Assignees: TERUMO KABUSHIKI KAISHA, Shibuya, Tokyo (JP); TEIKOKU SEIYAKU CO., LTD., Higashikagawa-Shi, Kagawa (JP)

(*) Notice: Subject to any disclaimer, the term of this patent is extended or adjusted under 35 U.S.C. 154(b) by 1162 days.

(21) Appl. No.: 13/578,168

(22) PCT Filed: Feb. 9, 2011

(86) PCT No.: PCT/JP2011/052730
§ 371 (c)(1),
(2), (4) Date: Aug. 9, 2012

(87) PCT Pub. No.: WO2011/099512
PCT Pub. Date: Aug. 18, 2011

(65) Prior Publication Data
US 2012/0310143 A1  Dec. 6, 2012

(30) Foreign Application Priority Data
Feb. 12, 2010 (JP) ................... 2010-028553

(51) Int. Cl.
*A61N 1/30* (2006.01)
*A61N 1/04* (2006.01)

(52) U.S. Cl.
CPC .................. *A61N 1/0428* (2013.01)

(58) Field of Classification Search
CPC ........ A61N 1/0448; A61N 1/044; A61N 1/30; A61N 1/325; A61N 1/0436; A61N 1/0428; A61N 1/18; A61N 1/0412; A61N 1/0416; A61N 1/0432; A61N 1/048; A61M 2037/0007; A61M 2205/055

(Continued)

(56) References Cited

U.S. PATENT DOCUMENTS 4,474,570 A    10/1984 Ariura et al.
5,562,607 A *  10/1996 Gyory ................. A61N 1/0436
                                                        439/188

(Continued)

FOREIGN PATENT DOCUMENTS

EP    1 911 489 A1    4/2008
JP    58-10066 A      1/1983

(Continued)

OTHER PUBLICATIONS

Office Action (Rejection of the Application) issued on Oct. 21, 2014, by the Japanese Patent Office in corresponding Japanese Patent Application No. 2011-553862 and an partial English translation of the Office Action. (4 pgs).

(Continued)

*Primary Examiner* — Bhisma Mehta
*Assistant Examiner* — Bradley G Thomas, Jr.
(74) *Attorney, Agent, or Firm* — Buchanan Ingersoll & Rooney PC

(57) ABSTRACT

An iontophoresis patch is equipped with a donor gel and a reference gel which are disposed to contact an external conductor, for example, the skin of a patient and thereby output current from a current-carrying device to the external conductor. The iontophoresis patch includes: a donor portion having the donor gel containing a medical agent to be penetrated into the external conductor; a reference portion having a reference gel, mounted with the current-carrying device on the surface on the side opposite to the reference gel, and disposed on the external conductor apart from the donor portion; and an electrode film for supplying current from the current-carrying device to the donor gel and the reference gel.

6 Claims, 11 Drawing Sheets

(58) Field of Classification Search
USPC .......................................................... 604/20
See application file for complete search history.

(56) References Cited

U.S. PATENT DOCUMENTS

| | | | |
|---|---|---|---|
| 6,377,848 B1* | 4/2002 | Garde .................... | A61N 1/30 604/20 |
| 6,587,717 B1 | 7/2003 | Kuribayashi et al. | |
| 2005/0228335 A1* | 10/2005 | Reddy ................ | A61N 1/0448 604/20 |
| 2008/0188779 A1* | 8/2008 | Vallero ................ | A61M 5/422 601/21 |
| 2009/0048556 A1 | 2/2009 | Durand | |

FOREIGN PATENT DOCUMENTS

| | | |
|---|---|---|
| JP | 9-510387 A | 10/1997 |
| JP | 3267291 B | 3/2002 |
| JP | 2007-532193 A | 11/2007 |
| JP | 4154016 B2 | 9/2008 |
| WO | WO 95/25562 A1 | 9/1995 |
| WO | 2007/018171 A1 | 2/2007 |
| WO | WO 2009/026139 A1 | 2/2009 |

OTHER PUBLICATIONS

International Search Report (PCT/ISA/210) issued on Mar. 29, 2011, by the Japanese Patent Office as the International Searching Authority for International Application No. PCT/JP2011/052730.
Written Opinion (PCT/ISA/237) issued on Mar. 29, 2011, by the Japanese Patent Office as the International Searching Authority for International Application No. PCT/JP2011/052730.

\* cited by examiner

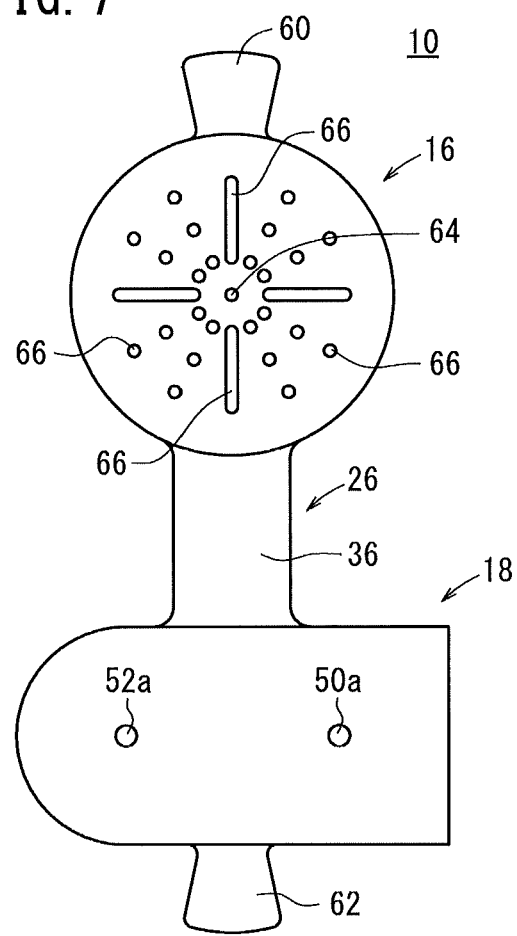

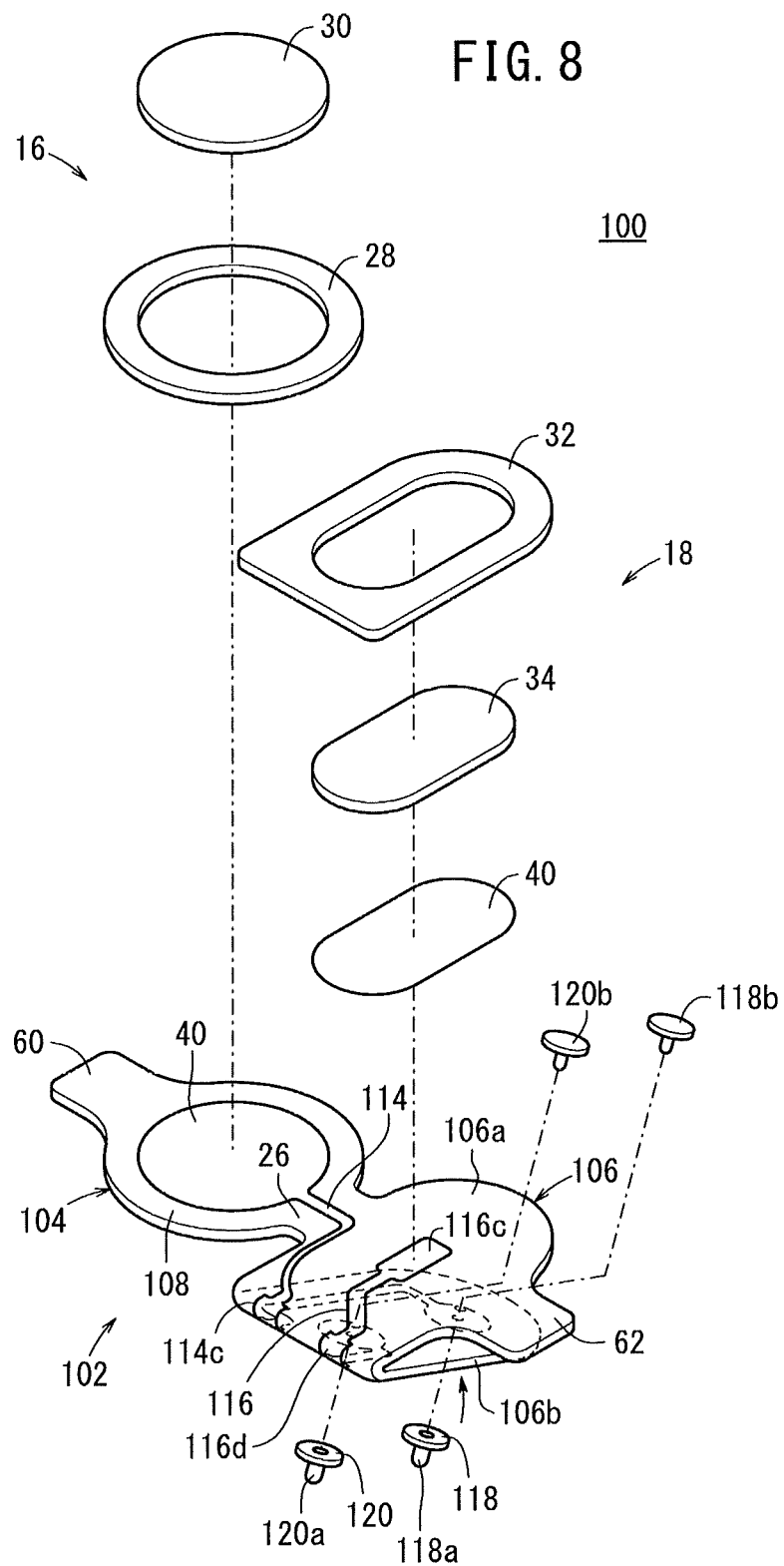

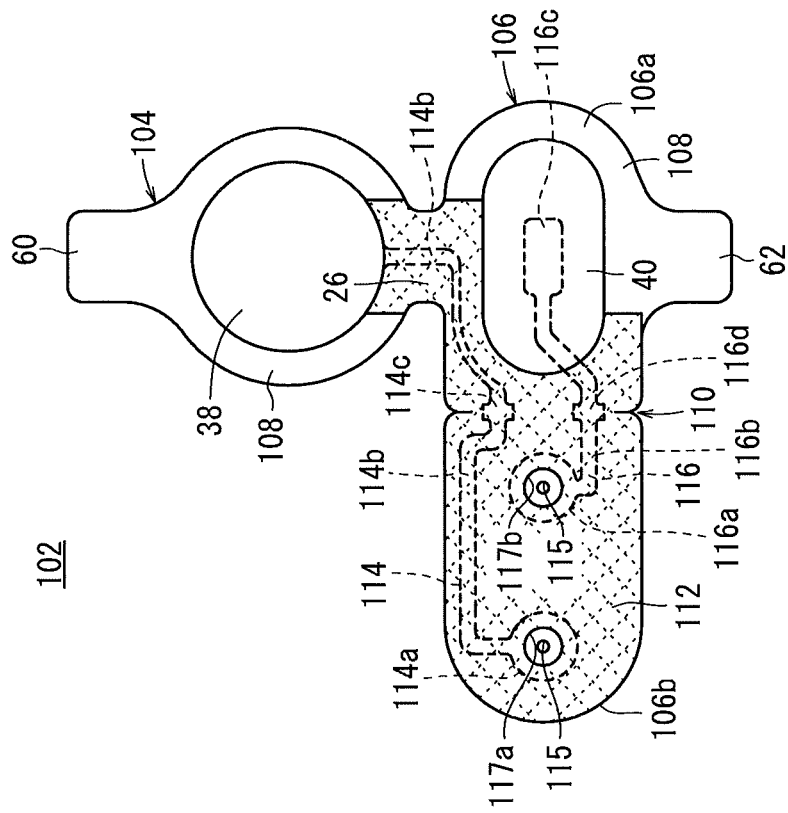
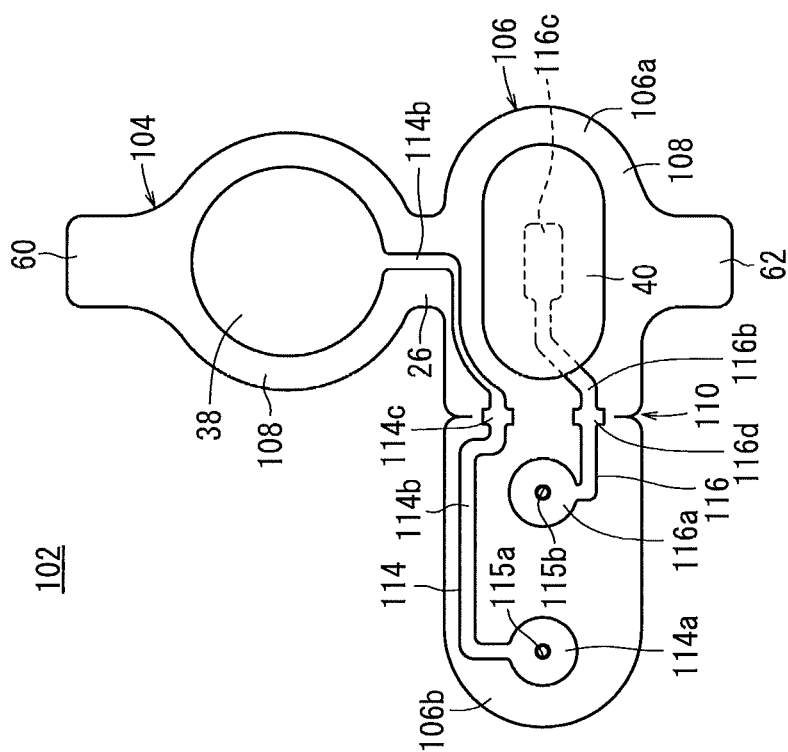

IONTOPHORESIS PATCH

TECHNICAL FIELD

The present invention relates to an iontophoresis patch for use with an ionic drug permeation device which operates on the principles of iontophoresis for transdermally administrating a drug such as a local anesthetic or the like by passing a low electric current through the skin of a human being.

BACKGROUND ART

Local anesthetic patches such as lidocaine are widely used for the purpose of removing a pain which is caused upon puncture. Particularly, local anesthetic patches find widespread use in hemodialysis. Hemodialysis patients are treated with dialysis three times a week, for example, by having two dialysis needles, each having a diameter ranging from 17 to 18 G (gauge), inserted through their skin for an extracorporeal blood circulation to remove waste materials from the blood. Such local anesthetic patches are used to remove the pain caused upon puncture.

Lidocaine patches take a long time, e.g., 2 hours, prior to the onset of their effect. Therefore, the skin area to which a lidocaine patch is applied is likely to be irritated. In addition, the efficacy of lidocaine patches tends to be insufficient because they fail to deliver the drug deeply into the tissue.

On the other hand, iontophoresis is advantageous in that it takes a shorter time until the onset of the drug efficacy and it can deliver the drug more deeply into the tissue. The above problems can be solved by combining local anesthetic patches such as lidocaine with iontophoresis. Specifically, iontophoresis refers to a process wherein positive and negative electrodes are placed at two spaced points on a skin and an electric current is passed from one of the electrodes across the stratum corneum to the other electrode thereby to move a charged drug based on the principle of electrophoresis for facilitating transdermal drug absorption. Iontophoresis provides a basis for a transdermal drug administration system. Usually, one of the positive and negative electrodes is held in contact with a gel containing the drug and referred to as a donor portion, and the other electrode is held in contact with a gel containing salt solution and referred to as a reference portion.

According to iontophoresis, the charged drug is subjected to facilitation of absorption in principle. There has been a report stating that since a water flow is developed in the patient's body due to an electric current, even a non-charged drug or even a high-molecular-weight drug exhibits increased skin permeability.

Japanese Laid-Open Patent Publication No. 2007-532193 (PCT) discloses an electrically assisted delivery device utilizing iontophoresis which includes an electrode assembly having positive and negative electrodes containing a drug and a controller for supplying an electric current to the electrode assembly. The disclosed electrically assisted delivery device is problematic in that it is not small enough to make the controller integral with a patch and is highly costly.

Japanese Laid-Open Patent Publication No. 09-510387 (PCT) discloses an electrically operated administration device having a structure wherein a flexible substrate and a button cell for energizing a pair of electrode means to be applied to the skin of a patient are disposed on upper portions of the electrode means.

SUMMARY OF INVENTION

The structure disclosed in Japanese Laid-Open Patent Publication No. 09-510387 (PCT) is reduced in size to a certain extent because the button cell and the flexible substrate are employed to make an energizing unit integral with a patch to be applied to the skin. However, since the substrate and the cell are stacked on the entire surface of the patch in planar view, the patch is inflexible in its entirety. Particularly, like a hemodialysis patient, if the blood vessel in a puncture area (shunt portion on an arm) is highly raised from the puncture area, then it is difficult to apply the inflexible patch in fully intimate contact with the raised blood vessel.

The present invention has been made in view of the above problems. It is an object of the present invention to provide an iontophoresis patch which is flexible enough to be stably placed on a raised portion of an external conductor such as a human skin or the like.

According to the present invention, there is provided an iontophoresis patch having a first contact member and a second contact member for outputting an electric current from an energizing unit to an external conductor upon being placed in contact with the external conductor, comprising a donor portion having the first contact member, the first contact member containing a drug to permeate into the external conductor, a reference portion having the second contact member and which is placed on the external conductor away from the donor portion, the energizing unit being placed on a surface of the second contact member which is opposite to a surface thereof to be held in contact with the external conductor, and an electrode body having a first electrode and a second electrode for supplying electric currents from the energizing unit respectively to the first contact member and the second contact member, the electrode body being disposed over the donor portion and the reference portion.

With the above arrangement, the iontophoresis patch has the donor portion which holds a drug to permeate into the external conductor, e.g., a human body, the reference portion disposed away from the donor portion, and the electrode body having the first electrode and the second electrode for supplying electric currents to the first contact member and the second contact member, the energizing unit being placed on the reference portion. Thus, since the energizing unit is not placed on the donor portion which holds the drug, the donor portion is more flexible than the reference portion. Therefore, even with respect to, for example, a skin of a hemodialysis patient having a highly raised blood vessel, the donor portion with the drug can easily conform closely to the shape of such a skin, and thus the donor portion can be placed stably in intimate contact with the skin of the hemodialysis patient.

The electrode body may have a one-sided interconnect structure in the donor portion wherein the first electrode is disposed on one surface of a flexible base, and the electrode body has a double-sided interconnect structure in the reference portion wherein the second electrode is disposed on a surface of the base, while a first contact terminal line and a second contact terminal line for interconnecting the energizing unit and the first electrode and the second electrode are disposed on another surface of the base. Thus, since the donor portion is thinner and more flexible than the reference portion, the donor portion can be held in increased intimate contact with the external conductor.

The electrode body may have a one-sided interconnect structure in the donor portion wherein the first electrode is disposed on one surface of a flexible bas, and the electrode body may have a double-sided interconnect structure in the reference portion wherein after the second electrode, and a first contact terminal line and a second contact terminal line for interconnecting the energizing unit and the first electrode and the second electrode are formed on the same surface of the base as the surface on which the first electrode is disposed, the base in the reference portion is folded back on itself into a two-layer structure, so that the second electrode is disposed on a surface of the reference portion, and terminal bases connecting the first contact terminal line and the second contact terminal line to the energizing unit are disposed on another surface of the reference portion. Thus, since the reference portion can be made into a double-sided interconnect structure simply by performing an interconnect forming process on one side of the base, the production efficiency is increased.

The first contact terminal line and the second contact terminal line include wider portions disposed on a portion of the reference portion that includes a folding portion of the base, the wider portions being wider than other portions of the first contact terminal line and the second contact terminal line. When the base is folded back on itself along the folding portion, the wider portions are effective to prevent the first contact terminal line and the second contact terminal line from being broken or buckled. Thus, the first contact terminal line and the second contact terminal line are made more durable and reliable.

The iontophoresis patch may include a bridge portion interconnecting the donor portion and the reference portion, wherein the first electrode and the first contact terminal line are electrically connected to each other in the bridge portion, and the second electrode and the second contact terminal line are electrically connected to each other in the bridge portion. Owing thereto, joints between the interconnections, e.g., through holes, are not disposed in the donor portion and the reference portion. Therefore, the electrode body in the donor portion and the reference portion can be made flat, thereby providing increased intimate contact between the first contact member and the second contact member, and the first electrode and the second electrode.

It is effective to provide a protective layer covering and electrically insulating the bridge portion for reliably insulating the joints between the interconnections.

The first contact terminal line connected to the first electrode and the second contact terminal line connected to the second electrode may be juxtaposed on the surfaces of the bridge portion and the reference portion, and the contact terminal lines may have respective ends electrically connected respectively to the first electrode and the second electrode in the bridge portion and respective other ends electrically connected respectively to connection terminals connected to the energizing unit in the reference portion. With this arrangement, the one-sided interconnect structure in the donor portion can be constructed more easily, and the electrode body can be reduced in outer shape for making the iontophoresis patch smaller in size.

The iontophoresis patch may include a manually grippable grip projectingly formed on a side of at least one of the donor portion and the reference portion. The applier can grip the grip to apply the iontophoresis patch more easily to the external conductor.

The donor may have, on a surface thereof opposite from the first contact member, a central mark indicative of the center of the first contact member as viewed in plan and an angle mark indicative of a rotational angle of the first contact member as viewed in plan. For example, the central mark allows the applier to apply the first contact member holding the drug to the external conductor more easily at a desired area of the external conductor. Owing to the angle marks, after determining the position to which the donor portion is to be applied, and when determining a position to which the reference portion is to be applied, the applier can turn the reference portion around the center of the angle mark to make it possible to apply the reference portion to a more stable position. Further, the supervisor can easily and accurately instruct the applier as to a position where to apply the reference portion.

According to the present invention, the iontophoresis path includes the donor portion holding the drug to permeate into the external conductor, e.g., a human body, the reference portion disposed away from the donor portion, and the electrode body having the first electrode and the second electrode for supplying electric currents to the first contact member and the second contact member, the energizing unit being placed on the reference portion. Thus, since the energizing unit is not placed on the donor portion which holds the drug, the donor portion is more flexible than the reference portion. Therefore, even with respect to, for example, a skin of a hemodialysis patient having a highly raised blood vessel, the donor portion with the drug can easily conform closely to the shape of such a skin, and thus the donor portion can be placed stably in intimate contact with the skin of the hemodialysis patient.

BRIEF DESCRIPTION OF DRAWINGS

FIG. 7 is a plan view of a modification of the iontophoresis patch shown in FIG. 1;

FIG. 8 is an exploded perspective view of an iontophoresis patch according to a second embodiment of the present invention;

FIG. 9A is a bottom plan view of an electrode film shown in FIG. 8 before a reference-side region thereof is folded back on itself;

FIG. 9B is a bottom plan view of the electrode film shown in FIG. 9A with an insulative resist layer placed on the face side thereof;

DESCRIPTION OF EMBODIMENTS

Iontophoresis patches according to preferred embodiments of the present invention in connection with an ionic drug permeation device which can incorporate such an iontophoresis path will be described in detail below with reference to the accompanying drawings.

Figure 1:
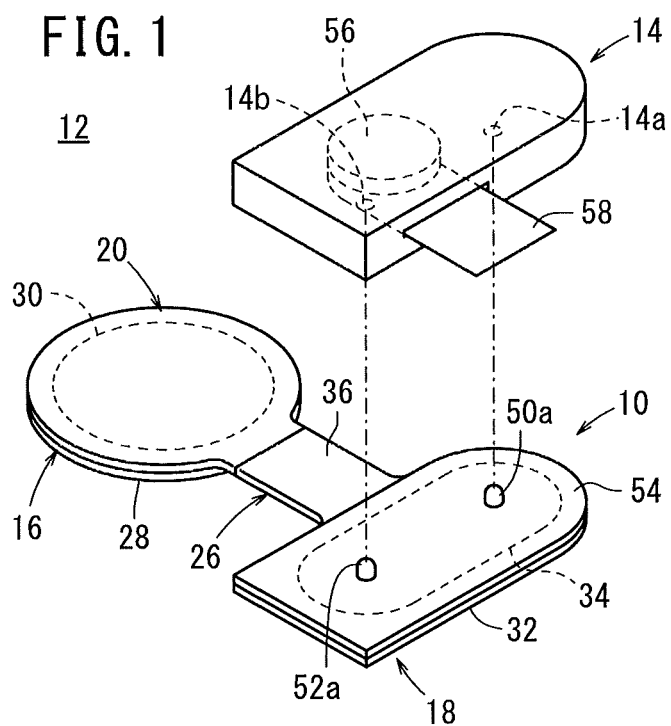
FIG. 1 is a perspective view showing the overall configuration of an ionic drug permeation device incorporating therein an iontophoresis patch according to a first embodiment of the present invention.
Figure 2:
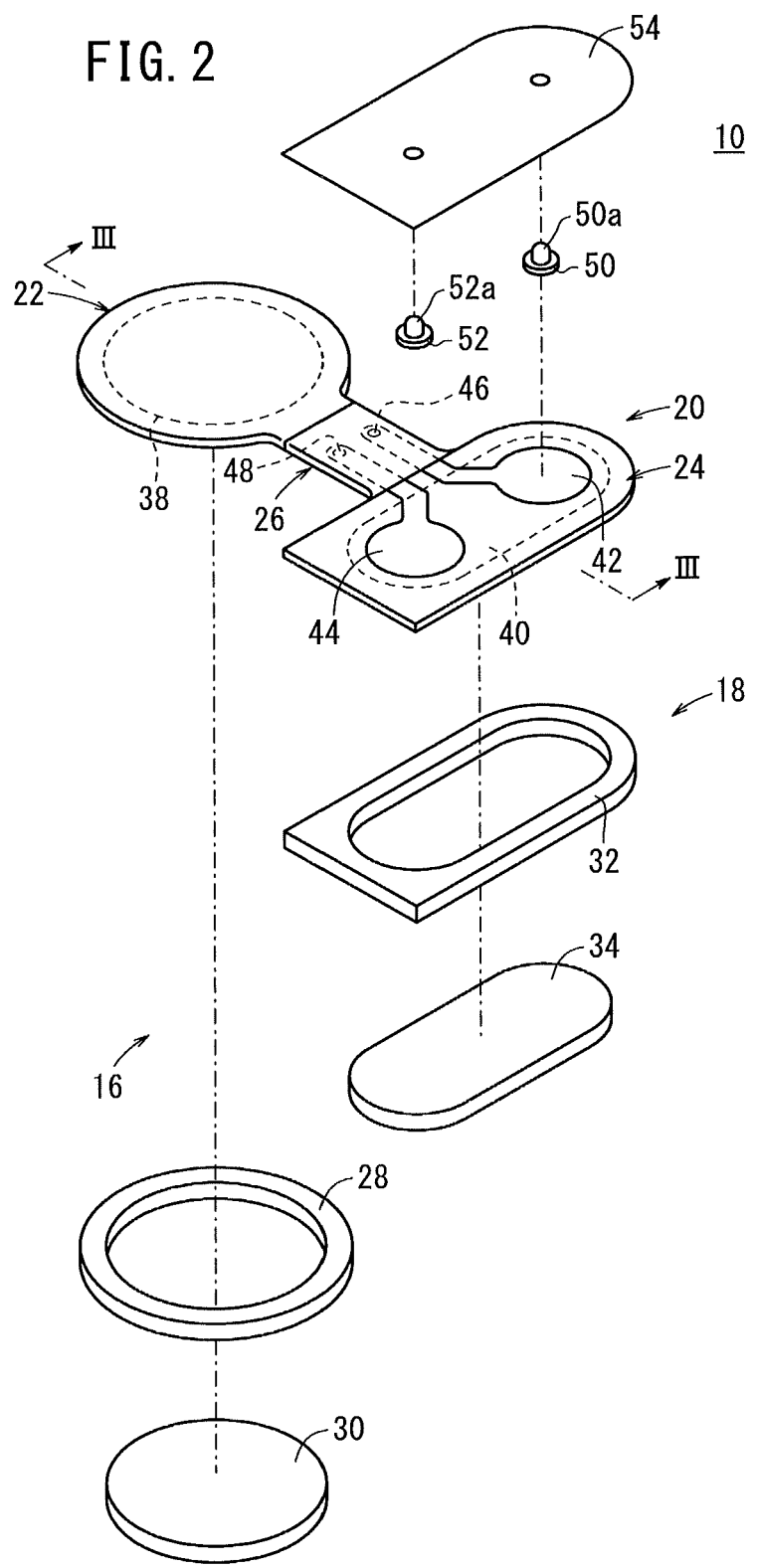
FIG. 2 is an exploded perspective view of the iontophoresis patch shown in FIG. 1.

FIG. 1 shows in perspective the overall configuration of an ionic drug permeation device 12 incorporating therein an iontophoresis patch 10 according to a first embodiment of the present invention. In FIG. 1, the iontophoresis patch 10 and an energizing unit 14, which jointly make up the ionic drug permeation device 12, are shown as separate from each other. FIG. 2 shows in exploded perspective the iontophoresis patch 10 shown in FIG. 1.

The ionic drug permeation device 12 (hereinafter also referred to as "device 12") is a medical instrument used to remove a pain caused upon puncture on a hemodialysis patient, for example, and also to administer a local anesthetic, e.g., an ionic anesthetic including lidocaine, to permeate into a patient's arm. The iontophoresis patch 10 (hereinafter also referred to as "patch 10") is applied to the skin of the patient, which is an external conductor, and is energized by the energizing unit 14 to cause the ionic anesthetic included in the patch 10 into the living body. The patch 10 may be applied to a device for administrating a drug other than the ionic anesthetic to a patient, and may be used for iontophoresis to deliver various drugs.

As shown in FIGS. 1 and 2, the device 12 includes the patch 10 and the energizing unit 14 placed on and connected to the face side (upper surface) of the patch 10.

The patch 10 has a donor portion 16 in the form of a circular thin sheet (film) and a reference portion 18 in the form of a rectangular thin sheet (film) with an arcuate side, the reference portion 18 being spaced from the donor portion 16. An electrode film (electrode body) 20 connected to the energizing unit 14 is placed over the donor portion 16 and the reference portion 18. The electrode film 20 includes a donor-side region 22 and a reference-side region 24 (see FIG. 2) which are shaped coextensively with the donor portion 16 and the reference portion 18, respectively, and a narrow bridge portion 26 disposed between the donor-side region 22 and the reference-side region 24 and joining the donor portion 16 and the reference portion 18.

The donor portion 16 has a circular donor application member 28 corresponding in shape to the outer shape of the donor portion 16, and a donor gel (first contact member) 30 which fills an opening defined in the donor application member 28. The donor-side region 22 of the electrode film 20 is electrically connected to the surface (upper surface in FIG. 2) of the donor gel 30. The reference portion 18 has a reference application member 32 of an oblong shape substantially corresponding in shape to the outer shape of the reference portion 18 and a reference gel (second contact member) 34 which fills an opening defined in the reference application member 32. The reference-side region 24 of the electrode film 20 is electrically connected to the surface (upper surface in FIG. 2) of the reference gel 34.

Each of the donor application member 28 and the reference application member 32 is made of a sticky elastic material which can adhere to a human skin or the like with a certain strength, and is electrically insulative. The donor gel 30 contains therein the ion anesthetic, and the reference gel 34 contains therein a solvent or a solution of an electrolyte, e.g., buffer salt, common salt, or the like, which is not harmful to living bodies, such as saline. Since a medical professional with sufficient puncture skills finds it easy to insert a needle into a puncture area of 2.5 (cm$^2$) for drug delivery, the surface (lower surface in FIG. 2) of each of the donor gel 30 and the reference gel 34 for contact with the skin should be of an area of about 2.5 (cm$^2$).

The donor gel 30 is inserted into the opening in the donor application member 28 and the reference gel 34 is inserted into the opening in the reference application member 32.

Then, the donor application member 28 and the reference application member 32 are applied to the skin of a patient, thereby bringing the donor portion 16 and the reference portion 18 substantially simultaneously into contact with the skin. Therefore, the patch 10 can simply be applied to the skin in one operation. The surfaces of the donor gel 30 and the reference gel 34 for contact with the skin may be made sticky.

Figure 3:
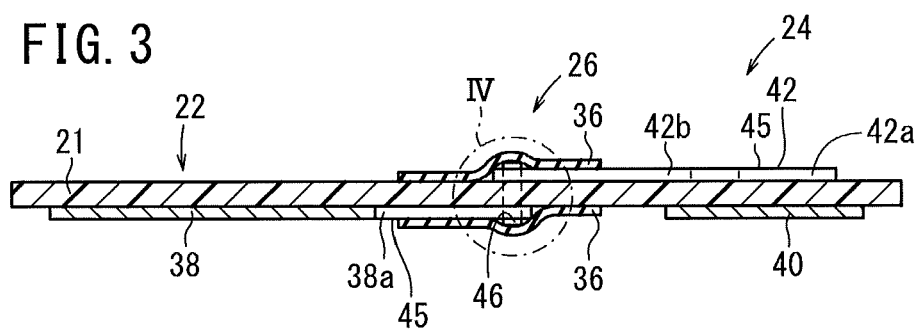
FIG. 3 is a cross-sectional view of an electrode film taken along line III-III of FIG. 2.
Figure 4:
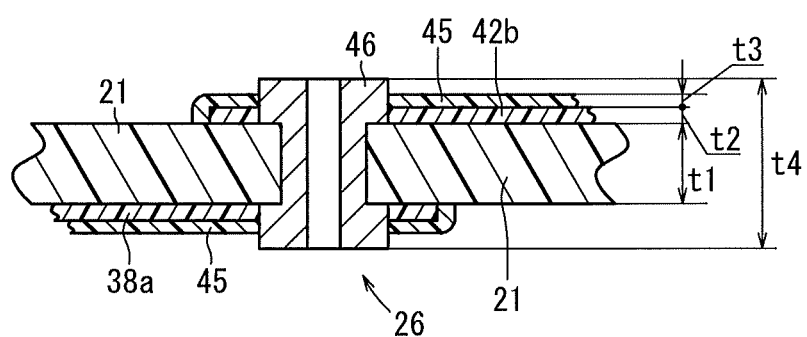
FIG. 4 is an enlarged cross-sectional view of portion IV encircled by the broken line in FIG. 3.
Figure 5B:
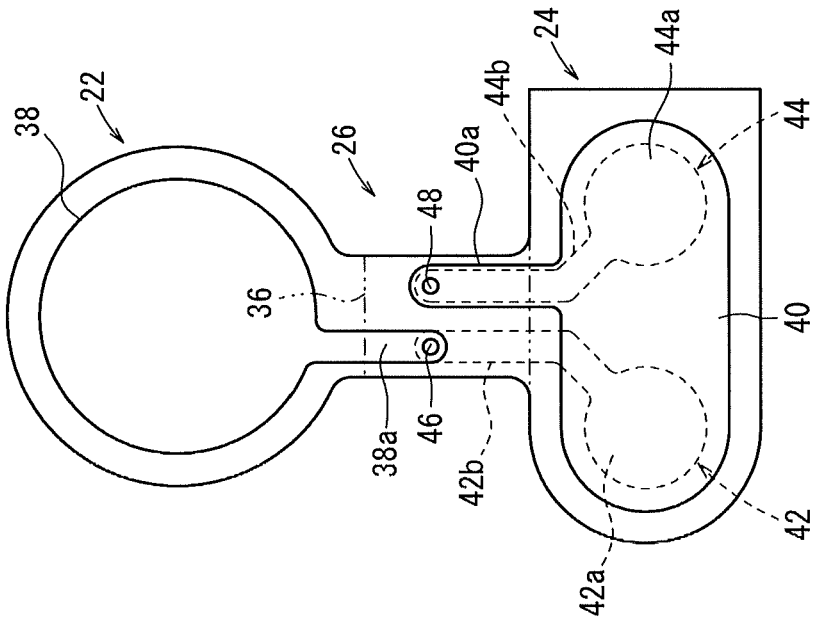
FIG. 5B is a bottom plan view of the electrode film.
Figure 5A:
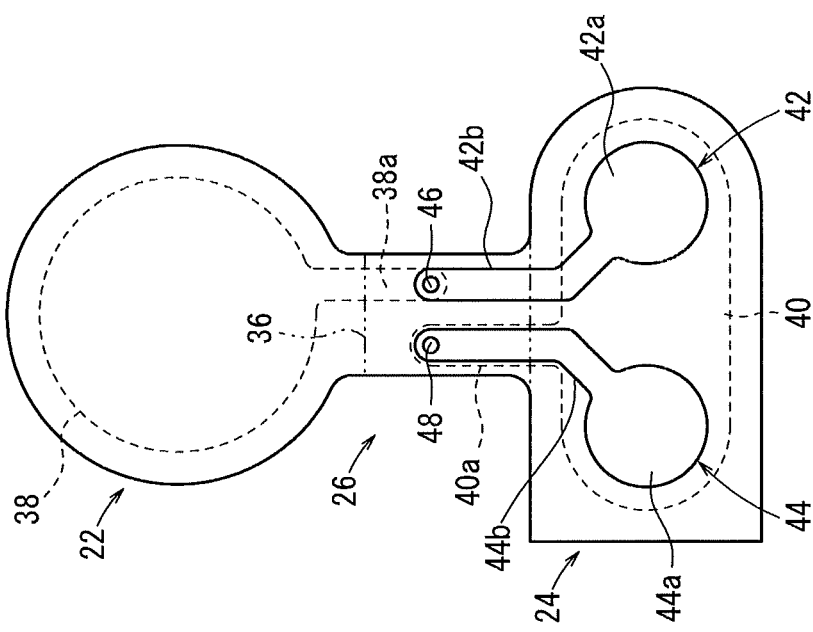
FIG. 5A is a plan view of the electrode film.

FIG. 3 is a cross-sectional view of the electrode film 20 taken along line III-III of FIG. 2. For an easier understanding of the electrode film 20, the thickness of the electrode film 20 is illustrated as exaggerated. FIG. 4 is an enlarged cross-sectional view of portion IV encircled by the broken line in FIG. 3. FIG. 5A is a plan view (top plan view) of the electrode film 20, and FIG. 5B is a bottom plan view of the electrode film 20. In FIGS. 4, 5A, and 5B, a cover lay 36 to be described later is omitted from illustration for an easier understanding of the electrode film 20.

The electrode film 20 comprises a flexible substrate having a flexible base 21 which defines the outer shape thereof and which includes portions constructed respectively as the donor-side region 22, the reference-side region 24, and the bridge portion 26. The base 21 comprises, for example, a thin flexible film of a resin such as polyester, polyimide, or the like.

As shown in FIGS. 3 through 5B, the donor-side region 22 includes a circular first electrode 38 disposed on the bottom surface of the base 21 and held in contact with and electrically connected to the donor gel 30. A connection line 38a extends from the first electrode 38 along one side of the bridge portion 26 to a substantially central portion thereof.

The reference-side region 24 includes an oblong second electrode 40 disposed on the bottom surface of the base 21 and held in contact with and electrically connected to the reference gel 34. A first contact terminal line 42 and a second contact terminal line 44 are juxtaposed on the surface of the base 21. A connection line 40a extends from the second electrode 40 along one side of the bridge portion 26 to the substantially central portion thereof in parallel to the connection line 38a (see FIG. 5B). The first and second contact terminal lines 42, 44 have a pair of respective circular terminal bases 42a, 44a juxtaposed on the face side of the reference-side region 24 and a pair respective connection lines 42b, 44b extending from the terminal bases 42a, 44a and bent to the substantially central portion of the bridge portion 26 parallel to each other.

The interconnections of the electrode film 20, i.e., the first electrode 38 (connection line 38a), the second electrode 40 (connection line 40a), and the first and second contact terminal lines 42, 44 (connection lines 42b, 44b, terminal bases 42a, 44a), are formed, for example, by printing an electrically conductive ink containing silver/silver chloride on the face side and reverse side of the base 21. The interconnections have exposed surfaces sealed by an electrically insulative adhesive 45 (see FIGS. 3 and 4). However, the bottom surfaces (contact surfaces) of the first electrode 38 and the second electrode 40 which are held in contact with the donor gel 30 and the reference gel 34 are not coated with the adhesive 45 (see FIG. 5B). The electrically conductive ink may have its thickness increased by being printed in a plurality of layers for reliably preventing conduction failures from occurring.

As shown in FIGS. 3 through 5B, the connection line 38a of the first electrode 38 and the connection line 42b of the first contact terminal line 42 are aligned with each other in the thicknesswise direction of the bridge portion 26 (see FIGS. 3 and 5B), and have their respective distal ends electrically connected to each other by a through hole 46 which extends through the bridge portion 26 in the thicknesswise direction thereof (see FIG. 4). Similarly, the connection line 40a of the second electrode 40 and the connection line 44b of the second contact terminal line 44 are aligned with each other in the thicknesswise direction of the bridge portion 26, and have their respective distal ends electrically connected to each other by a through hole 48 which extends through the bridge portion 26 in the thicknesswise direction thereof.

With the electrode film 20, as described above, the base 21 of the donor-side region 22 is of a one-sided interconnect structure having the first electrode 38 only, and the base 21 of the reference-side region 24 is of a double-sided interconnect structure having the second electrode 40, the first contact terminal line 42 and the second contact terminal line 44. Therefore, the donor portion 16 including the donor-side region 22 of the one-sided interconnect structure is more flexible than the reference portion 18 including the reference-side region 24 of the double-sided interconnect structure. The bridge portion 26 has the various interconnects and the through holes 46, 48 lumped together on its substantially central portion. However, since the bridge portion 26 is of the one-sided interconnect structure having the connection line 38a only near the donor-side region 22, the bridge portion 26 is also flexible near the donor portion 16.

As shown in FIGS. 2 and 3, the bridge portion 26 is surrounded by cover lays (protective layers) 36, each in the form of an electrically insulative sheet, for preventing the connection lines 38a, 40a, 42b, 44b and the through holes 46, 48 from being exposed outwardly. Instead of the cover lays 36, electrically insulative coatings (resist layers) may be used. However, if the bridge portion 26 should have more flexibility and durability, then the cover lays 36 in the form of sheets are more effective.

As shown in FIG. 4, the electrode film 20 comprises a thin film wherein, for example, the base 21 has a thickness t1 ranging from 12.5 μm to 250 μm, preferably from about 12.5 μm to 50 μm, each of the interconnections made of an electrically conductive ink, such as the first electrode 38, the connection line 38a, etc. has a thickness t2 of about 20 μm, the adhesive 45 has a thickness t3 ranging from about 20 μm to 30 μm, and each of the through holes 46, 48 has a thickness t4 of about 140 μm. If the thickness of the donor portion 16 is represented by the sum of 25 μm as the thickness of the base 21, 20 μm as the thickness of the first electrode 38, and 20 μm as the thickness of the adhesive 45, then the donor portion 16 is of a thin shape that is sufficiently flexible.

The thickness t4 of the through holes 46, 48 tends to be the greatest in the entire electrode film 20. With the patch 10 according to the present embodiment, the through holes 46, 48 are disposed in the bridge portion 26, thereby making the donor-side region 22 and the reference-side region 24 flat by preventing them from having bulges which would otherwise be produced by through holes. Therefore, increased intimate contact is achieved between the donor gel 30 and the reference gel 34 and the first electrode 38 and the second electrode 40. Depending on the conditions in which the patch 10 is used, the through holes 46, 48 may be disposed in the donor-side region 22 or the reference-side region 24.

As shown in FIG. 2, connection terminals (hooks) 50, 52 are mounted on the respective terminal bases 42a, 44a that are electrically connected to the first electrode 38 and the second electrode 40, by respective electrically conductive members (e.g., silver paste). The connection terminals 50, 52 have respective projections 50a, 52a, each in the form of a small-diameter cylinder, projecting upwardly. The other portions of the connection terminals 50, 52 than the projections 50a, 52a, together with the terminal bases 42a, 44a, and the connection lines 42b, 44b are covered with an insulating film (hook cover) 54. The insulating film 54 has a pair of holes defined therein through which the projections 50a, 52a penetrate. With only the projections 50a, 52a being exposed from the insulating film 54, the face sides of the other members of the reference-side region 24 are covered with the insulating film 54.

As described later in a second embodiment, by use of fasteners (grommets), the connection terminals may be fixed to the base by crimping the connection terminals and the fasteners with the base sandwiched therebetween.

As shown in FIG. 1, the energizing unit 14 has connection holes 14a, 14b defined in the bottom surface thereof for connection to the projections 50a, 52a of the connection terminals 50, 52. The energizing unit 14 houses therein two series-connected cells 56 and an electric circuit which comprises a plurality of parallel-connected constant-current diodes, not shown.

The energizing unit 14 includes an insulating sheet 58 held against the cathode of the cells 56. Prior to use of the device 12, the insulating sheet 58 prevents an electric current from flowing from the cells 56 to the constant-current diodes. When the device 12 stars to be used, the insulating sheet 58 is pulled away to electrically connect the cathode of the cells 56 to the electrode film 20. An electric current then flows from the cells 56 through the electrode film 20 to the donor gel 30, the body of the patient, and the reference gel 34. Alternatively, a power supply switch may be used instead of the insulating sheet 58.

The device 12 thus constituted provides a current path along which the energizing unit 14 supplies an electric current from the connection terminal 50 connected to the connection hole 14a through the terminal base 42a, the connection line 42b, the connection line 38a, and the first electrode 38 to the donor gel 30, and the electric current supplied to the donor gel 30 flows through the body of the patient, the reference gel 34, the second electrode 40, the connection line 40a, the connection line 44b, the terminal base 44a, and the connection terminal 52, and then from the connection hole 14b back to the energizing unit 14.

The patch 10 according to the present embodiment has the first contact terminal line 42, the second contact terminal line 44, and the connection terminals 50, 52 for connecting and placing the energizing unit 14, only on the face side of the reference portion 18.

Figure 6:
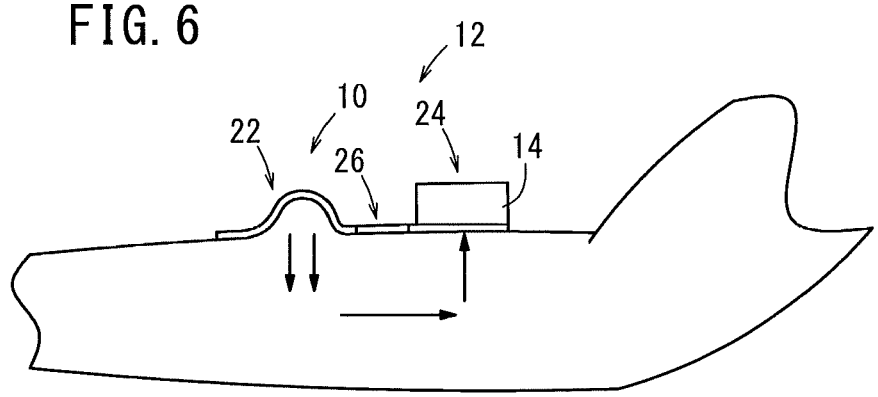
FIG. 6 is a side elevational view showing the manner in which the ionic drug permeation device shown in FIG. 1 is placed in intimate contact with a patient's arm.

Therefore, of the pair of gels functioning as a pair of electrodes to be applied to the skin of the patient, the donor portion 16 including the donor gel 30 which holds the drug is free of the energizing unit 14, and hence has its flexibility not impaired by the energizing unit 14. Therefore, as shown in FIG. 6, the donor portion 16 which contains the drug can easily conform closely to surface irregularities of a patient's arm or a highly raised blood vessel of a hemodialysis patient and thus the donor portion 16 can be secured in intimate contact with the surface irregularities of the patient's arm or the highly raised blood vessel of the hemodialysis patient. Since the donor portion 16 and the reference portion 18 are spaced from each other with the bridge portion 26 interposed therebetween, the donor portion 16 is highly flexible for better freedom with which to apply itself to the patient's body. Furthermore, as the energizing unit 14 can be connected directly to the patch 10, the device 12 is reduced in overall size and is easy to handle, advantageously.

The donor portion 16 and the reference portion 18 may be spaced from each other in a configuration without the bridge portion 26 being interposed therebetween. For example, the bridge portion 26 may be integral with the reference portion 18, and thus the bridge portion 26 may be omitted in appearance.

With respect to the electrode film 20 of the patch 10, the donor portion 16 is of a one-sided interconnect structure and the reference portion 18 is of a double-sided interconnect structure, thereby making the donor portion 16 thinner and more flexible than the reference portion 18 for more intimate contact with the patient.

With the patch 10, furthermore, the through holes 46, 48 which connect the first electrode 38 and the second electrode 40 that contact the donor gel 30 and the reference gel 34 with the first and second contact terminal lines 42, 44 that are connected to the energizing unit 14, i.e., connecting between the connection lines 38a, 40a and the connection lines 42b, 44b, are disposed in the bridge portion 26. Therefore, the donor-side region 22 and the reference-side region 24 of the electrode film 20 are made flat by preventing them from having bulges which would otherwise be produced by through holes. Therefore, increased intimate contact is achieved between the donor gel 30 and the first electrode 38, and between the reference gel 34 and the second electrode 40, thereby for preventing conduction failures from occurring.

Since the first contact terminal line 42 connected to the first electrode 38 and the second contact terminal line 44 connected to the second electrode 40 are disposed parallel to each other on the face sides of the bridge portion 26 and the reference portion 18, the one-sided interconnect structure can be easily provided on the donor portion 16, and the electrode film 20 can be smaller in outer shape.

As shown in FIG. 7, the patch 10 may have grips 60, 62, each in the form of a small ear-shaped member, projecting on respective outer side surfaces of the donor portion 16 and the reference portion 18. The grips 60, 62 are shaped so as to be easily gripped by the index fingers and thumbs of the right and left hands of a doctor, a nurse, or the like who applies the patch 10 to the patient, for example. Owing to the grips, when the applier applies the patch 10 to the skin of the patient, its fingertips are prevented from touching the donor gel 30, the reference gel 34, the donor application member 28, and the reference application member 32, and hence the adhering capability of the patch 10 is prevented from being lowered before the patch 10 is applied. When the patch 10 is to be applied, the applier may lightly pull the patch 10 in directions to space the donor portion 16 and the reference portion 18 apart from each other, thereby elongating the patch 10 straight to make it possible to bring the patch 10 accurately and easily into intimate contact with a target area.

As shown in FIG. 7, the patch 10 may have, on the face side of the donor portion 16, a central mark 64 indicative of the center of the donor gel 30 as viewed in plan and a plurality of angle marks 66 indicative of rotational angles of the donor gel 30 around the central mark 64. The central mark 64 and the angle marks 66 may be represented by electrically nonconductive characters and symbols drawn on the face side of the donor-side region 22 of the electrode film 20 by silk screen printing or ink jet printing. The central mark 64 and the angle marks 66 have a thickness of about 17 μm, for example. The angle marks 66 serve as, for example, radial spider lines angularly spaced at 30 degrees around the central mark 64.

The central mark 64 allows the applier to apply the patch 10 to the skin easily at a desired area of the skin by aligning the center of the donor gel 30 with the desired area. Owing to the angle marks 66, after determining the position to which the donor portion 16 is to be applied by using the central mark 64, and when determining a position to which the reference portion 18 is to be applied, the applier can turn the reference portion 18 around the central mark 64 to make it possible to apply the reference portion 18 to a more stable position. Further, the supervisor can easily and accurately instruct the applier as to a position where to apply the reference portion 18. As the energizing unit 14 is not placed on the donor portion 16, advantageously the central mark 64 and the angle marks 66 can easily be formed on the donor portion 16.

Only one of the central mark 64 and the angle marks 66 may be used, for example. In the case where the angle marks 66 are provided, even if the central mark 64 may be omitted, the center of the angle marks 66 may essentially function as a central mark.

The grips 60, 62, and the central mark 64 and the angle marks 66 may be provided altogether, as shown in FIG. 7. Alternatively, either one of the grips 60, 62, and the central mark 64 and the angle marks 66 may be used. If all of them are used as shown in FIG. 7, then advantageously while the applier is gripping the grips 60, 62, the applier can easily and stably position the patch 10 using the central mark 64 and the angle marks 66.

FIG. 8 shows in exploded perspective an iontophoresis patch 100 according to a second embodiment of the present invention.

As with the iontophoresis patch 10 according to the first embodiment, the iontophoresis patch 100 (hereinafter also referred to as "patch 100") according to the present embodiment, and the energizing unit 14 (see FIGS. 1 and 11) jointly make up an ionic drug permeation device. Those parts of the patch 100 according to the present embodiment which have identical or similar functions and advantages to those of the patch 10 according to the first embodiment are denoted by identical reference characters, and will not be described in detail below.

As shown in FIG. 8, the patch 100 is substantially the same as the patch 10 shown in FIG. 1, etc. in that it has a donor portion 16 in the form of a circular thin sheet (film) and a reference portion 18 in the form of a rectangular thin sheet (film) with an arcuate side, the reference portion 18 being joined to the donor portion 16 by a bridge portion 26. However, an electrode film (electrode body) 102 that is placed over the donor portion 16 and the reference portion 18 has structural details different from those of the electrode film 20 shown in FIGS. 1 through 5B.

The electrode film 102 includes a donor-side region 104 and a reference-side region 106 which are shaped so as to correspond to the donor portion 16 and the reference portion 18, respectively, and has an outer shape defined by a base 108 which has a single-layer structure in the donor-side region 104 and a double-layer structure (two-layer structure) in the reference-side region 106 which is folded back on itself along a folding portion (bending portion) 110. The reference-side region 106 comprises a first reference-side region 106a (bottom side) to be applied to the skin and a second reference-side region 106b which is folded along the folding portion 110 so as to overlap the reverse side of the first reference-side region 106a (see FIG. 8). With the electrode film 20 of the patch 10, the donor-side region 22 and the reference-side region 24 are formed by the base 21 which is of a single-layer structure (see FIG. 3).

In the donor portion 16 of the patch 100, the donor-side region 104 of the electrode film 102 is electrically connected to the face side (lower surface in FIG. 8) of the donor gel 30. Similarly, in the reference portion 18, the reference-side region 106 of the electrode film 102 is electrically connected to the face side (lower surface in FIG. 8) of the reference gel 34.

FIG. 9A is a bottom plan view of the electrode film 102 before the reference-side region 106 is folded back on itself, and FIG. 9B is a bottom plan view of the electrode film 102 shown in FIG. 9A with an insulative resist layer 112 placed on the face side thereof. Specifically, FIG. 9A is a bottom plan view of the electrode film 102 with the resist layer 112 (represented by the dashed cross-hatched pattern in FIG. 9B) omitted from illustration. In FIGS. 9A and 9B, most of the face side of the electrode film 102 (the donor-side region 104 and the first reference-side region 106a) is shown as a bottom surface to be applied to the skin. In an actual product, the second reference-side region 106b folded back along the folding portion 110 provides an upper surface on which the energizing unit 14 is placed.

As shown in FIG. 9A, the electrode film 102 before the reference-side region 106 is folded back on itself (while the assembly is in a production process) comprises a flexible substrate which has the single base 108 wherein the reference-side region 106 is of a symmetrical shape with respect to the folding portion 110. As with the base 21, the base 108 comprises a thin flexible film of a resin such as polyester, polyimide, or the like.

The single base 108 has an outer shape which is substantially L-shaped before the reference-side region 106 is folded back on itself. On the single base 108, various electrodes and interconnections of the donor-side region 104 and the reference-side region 106 are formed.

The donor-side region 104 includes a circular first electrode 38 disposed on the bottom surface of the base 108 and held in contact with and electrically connected to the donor gel 30. The reference-side region 106 includes an oblong second electrode 40 disposed on the bottom surface of the base 108 (the face side of the first reference-side region 106a). The first electrode 38 and the second electrode 40 are connected to the energizing unit 14 respectively by a first contact terminal line 114 and a second contact terminal line 116 which are wired on the base 108.

The first contact terminal line 114 includes a terminal base 114a disposed on the face side of the second reference-side region 106b and a connection line 114b extending from the terminal base 114a in a bent pattern along the face sides of the first reference-side region 106a and the bridge portion 26 and connected to the first electrode 38. The terminal base 114a has a small-diameter hole 115a defined centrally therein and extending therethrough in a thicknesswise direction thereof. The hole 115a also extends through the base 108.

The second contact terminal line 116 includes a terminal base 116a disposed on the face side of the second reference-side region 106b side by side with the terminal base 114a, and a connection line 116b extending from the terminal base 116a in a bent pattern to a substantially central area of the first reference-side region 106a so as to be connected to the second electrode 40. The connection line 116b has a small rectangular electrode mounting plate 116c on an end thereof remote from the terminal base 116a. The second electrode 40 is held in contact with the electrode mounting plate 116c in an electrically conductive state. As with the terminal base 114a, the terminal base 116a has a hole 115b defined centrally therein and extending therethrough and also through the base 108.

As shown in FIG. 9A, in the electrode film 102, the first electrode 38, the first contact terminal line 114, and the second contact terminal line 116 are formed by printing an electrically conductive ink containing silver, for example, on the face side of the base 108 before the reference-side region 106 is folded back on itself. After the electrode mounting plate 116c of the second contact terminal line 116 is formed, the second electrode 40 is formed by printing an electrically conductive ink containing silver/silver chloride on the upper surface of the electrode mounting plate 116c. The second electrode 40 may be made of the same material as the first electrode 38, etc. If the second electrode 40 is made of the same material as the first electrode 38, etc., then the electrode mounting plate 116c may be dispensed with, and the first electrode 38, the first contact terminal line 114, the second contact terminal line 116, and the second electrode 40 may be formed altogether.

The interconnections have exposed surfaces which is sealed, for example, by a resist layer 112 made of an electrically insulative adhesive, a coating, or the like, as shown in FIG. 9B after the first electrode 38, the first contact terminal line 114, and the second contact terminal line 116 have been formed. The surfaces of the first electrode 38 and the second electrode 40 which are held in contact with the donor gel 30 and the reference gel 34 are not coated with the resist layer 112, and holes 117a, 117b which are not coated with the resist layer 112 are defined around the respective holes 115a, 115b. The holes 117a, 117b are of a circular shape greater in diameter than the holes 115a, 115b. The electrically conductive ink may have its thickness increased by being printed in a plurality of layers for reliably preventing conduction failures from occurring. The exposed surfaces of the interconnections may be covered with an electrically insulative sheet applied thereto, instead of the resist layer 112.

The connection lines 114b, 116b of the first contact terminal line 114 and the second contact terminal line 116 have respective portions corresponding to the folding portion 110, i.e., respective portions including the folding portion 110, which are formed as wider portions 114c, 116d (see FIG. 9A) which are wider than the other portions of the connection lines 114b, 116b on both sides of the wider portions 114c, 116d. When the first reference-side region 106a and the second reference-side region 106b are folded back on each other along the folding portion 110, the wider portions 114c, 116d are effective to reliably prevent the connection lines 114b, 116b from being broken or buckled. Thus, the connection lines 114b, 116b can be made more durable and reliable at the time the first reference-side region 106a and the second reference-side region 106b are folded back on each other.

A process of constructing the patch 100 using the electrode film 102 thus constituted will be described below.

Figure 10A:
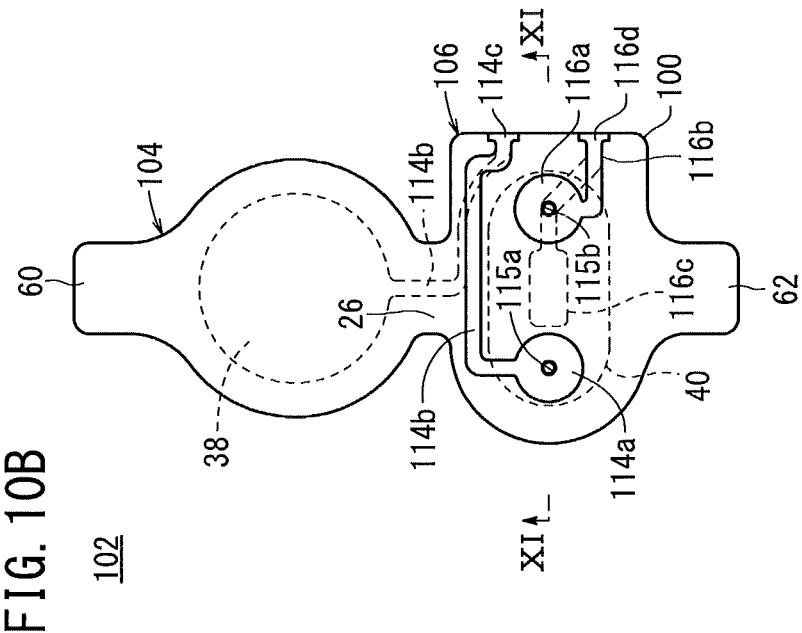
FIG. 10A is a bottom plan view of the electrode film shown in FIG. 9A after the reference-side region thereof is folded back on itself.
Figure 10B:
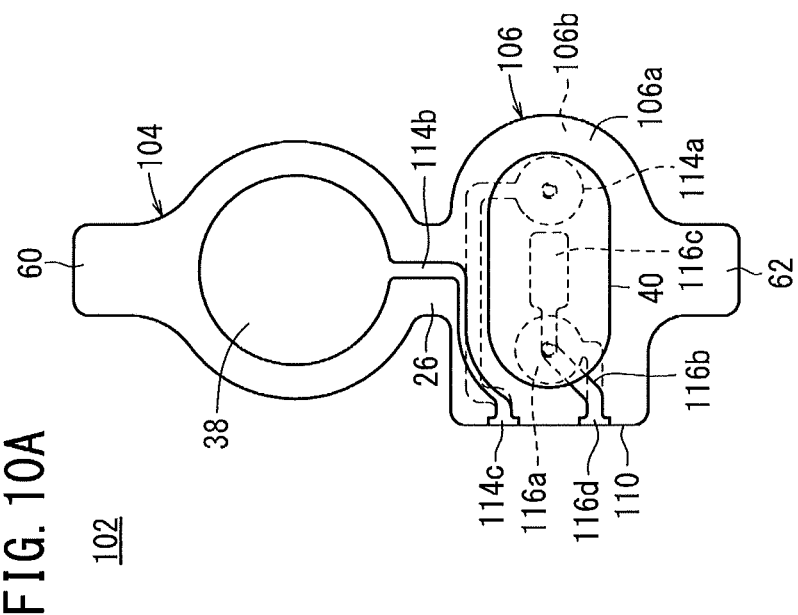
FIG. 10B is a plan view of the electrode film shown in FIG. 10A.

First, the first electrode 38, the second electrode 40, the first contact terminal line 114, and the second contact terminal line 116 are formed on one face of the base 108, and thereafter the reference-side region 106 is folded back on itself along the folding portion 110, as shown in FIGS. 10A and 10B. Then, the first reference-side region 106a and the second reference-side region 106b are fixed to each other by an adhesive or the like with their reverse sides held in close contact with each other. On the reference-side region 106, the second electrode 40 is disposed on the same surface as the surface on which the first electrode 38 is disposed (see FIG. 10A), and the terminal bases 114a, 116a are disposed on the other surface which is the reverse side thereof (see FIG. 10B).

Figure 11:
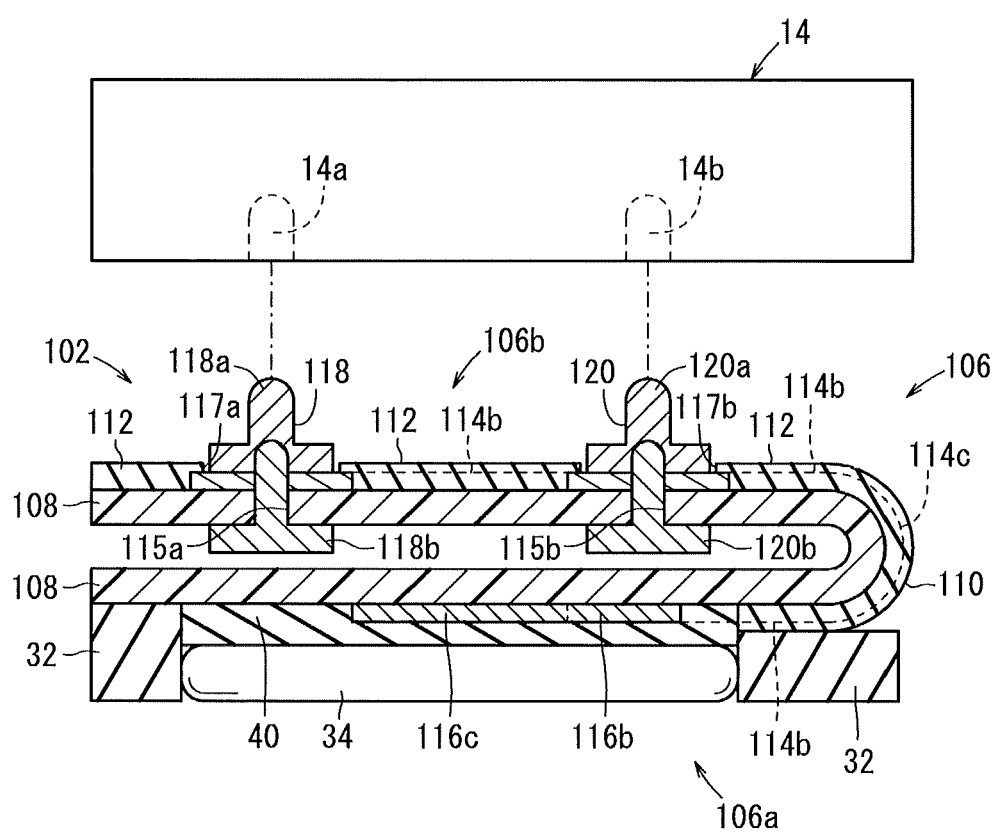
FIG. 11 is a cross-sectional view taken along line XI-XI of FIG. 10B.

Prior to the folding process, as shown in FIG. 11, connection terminals (hooks) 118, 120 are fixed to the upper surfaces of the respective terminal bases 114a, 116a by fasteners (grommets) 118b, 120b which are inserted from the reverse side of the base 108 into the respective holes 115a, 115b. The connection terminals (hooks) 118, 120 and the fasteners 118b, 120b are now securely fixed to the second reference-side region 106b, and the connection terminals 118, 120 are electrically connected to the terminal bases 114a, 116a. The connection terminals 118, 120 may be substantially identical in structure to the connection terminals 50, 52 (see FIG. 2) except that they have small holes in which the fasteners 118b, 120b are fitted. The connection terminals 118, 120 have projections 118a, 120a, respectively, each in the form of a small-diameter cylinder, projecting upwardly from their upper surfaces for connection to the connection holes 14a, 14b (see FIG. 1) of the energizing unit 14. In FIG. 11, for an easier understanding of the electrode film 102, the thickness of the electrode film 102 is illustrated as exaggerated, and the base 108 of the first reference-side region 106a and the base 108 of the second reference-side region 106b are illustrated as spaced from each other. Actually, however, the base 108 of the first reference-side region 106a and the base 108 of the second reference-side region 106b are held in intimate contact with each other.

Then, as shown in FIGS. 8 and 11, the donor application member 28, the reference application member 32, the donor gel 30, and the reference gel 34 are placed in respective given positions on the electrode film 102 folded back on itself as described above, thereby producing the patch 100.

The thus-constituted patch 100 provides a current path along which an electric current is supplied from the connection terminal 118 connected to the connection hole 14a of the energizing unit 14 through the terminal base 114a, the connection line 114b, and the first electrode 38 to the donor gel 30, and the electric current supplied to the donor gel 30 flows through the body of the patient, the reference gel 34, the second electrode 40, the electrode mounting plate 116c, the connection line 116b, the terminal base 116a, and the connection terminal 120, and then from the connection hole 14b back to the energizing unit 14. Thus, by using the patch 100, an ionic drug permeation device which can be used in substantially the same manner as the device 12 shown in FIG. 1 can be constituted.

When the patch 100 according to the present embodiment is manufactured, as shown in FIG. 9A, the interconnect forming process on the electrode film 102 can be finished simply by forming the first electrode 38, the second electrode 40, the first contact terminal line 114, and the second contact terminal line 116 on one surface of the base 108. Thereafter, the reference-side region 106 is folded back on itself along the folding portion 110, thereby producing the electrode film 102 of a desired constitution.

With the electrode film 20 of the patch 10 according to the first embodiment, it is necessary to perform the interconnect forming process on both surfaces of the base 21. In contrast thereto, with the electrode film 102 of the patch 100 according to the second embodiment, simply by performing the interconnect forming process on one surface of the base 108, and then folding the reference-side region 106 back on itself along the folding portion 110, the reference-side region 106 can be made into a double-sided interconnect structure. Therefore, the interconnect forming process is simplified for increased production efficiency, and the printing of the interconnections requires only one plate (original plate) for one-sided printing, and thus the cost thereof can be reduced.

As with the patch 10, the donor-side region 104 to be brought into intimate contact with a patient's arm can be of a flexible one-sided interconnect structure, thereby making it possible to bring the donor portion 16 into sufficiently intimate contact with the patient.

The folded-back structure of the reference-side region 106 of the patch 100 makes it unnecessary to provide the through holes 46, 48, etc. (see FIGS. 3 and 4) between the first electrode 38 and the second electrode 40, and the first and second contact terminal lines 114, 116 that are connected to the energizing unit 14. Consequently, the bridge portion 26 in particular is highly flexible, so that the ability of the patch 100 to be applied to the patient is further increased.

The patch 100 may also have not only the grips 60, 62 but also the central mark 64 and the angle marks 66 (see FIG. 7).

The present invention is not limited to the above embodiment, but may adopt various arrangements and processes without departing from the scope of the invention.

For example, the energizing unit 14 may be of another arrangement than the above arrangement insofar as it is capable of energizing the patches 10, 100 as desired.

The donor gel 30 and the reference gel 34, and the donor portion 16 and the reference portion 18 may be of shapes other than those described above, and their shapes may be changed depending on the applications and specifications of the patches 10, 100.

The invention claimed is:

1. An iontophoresis patch having a first contact member and a second contact member for outputting an electric current from an energizing unit to an external conductor upon being placed in contact with the external conductor, comprising:
    a donor portion having the first contact member, the first contact member containing a drug to permeate into the external conductor;
    a reference portion having the second contact member and which is placed on the external conductor away from the donor portion;
    an electrode body having a flexible base, and a first electrode and a second electrode which are disposed on the base, for supplying electric currents from the energizing unit respectively to the first contact member and the second contact member, the electrode body being disposed over the donor portion and the reference portion;
    a pair of connection terminals through which the energizing unit is disposed on the iontophoresis patch and which are electrically connected to the first electrode and the second electrode, wherein the pair of connection terminals are disposed on only the reference portion;
    wherein the electrode body has a one-sided interconnect structure in the donor portion wherein the first electrode is disposed on a surface of the base that faces the external conductor; and
    the electrode body has a double-sided interconnect structure in the reference portion wherein after the second electrode and a first contact terminal line and a second contact terminal line for interconnecting the pair of connection terminals and the first electrode and the second electrode are formed on the same surface of the base as the surface on which the first electrode is disposed, a portion of the base on which the first contact terminal line and the second contact terminal line are formed is folded back on itself into a two-layer structure, so that the second electrode is disposed on a surface of the reference portion that faces the external conductor, and terminal bases connected to the first contact terminal line and the second contact terminal line and also connected to the pair of connection terminals are disposed on a surface of the reference portion that is opposite to the surface thereof facing the external conductor.

2. The iontophoresis patch according to claim 1, wherein the first contact terminal line and the second contact terminal line include wider portions disposed on a portion of the reference portion that includes a folding portion of the base, the wider portions being wider than other portions of the first contact terminal line and the second contact terminal line.

3. The iontophoresis patch according to claim 1, wherein the electrode body includes a bridge portion interconnecting the donor portion and the reference portion.

4. The iontophoresis patch according to claim 3, comprising:
   a protective layer covering and electrically insulating the bridge portion.

5. The iontophoresis patch according to claim 1, comprising:
   a manually grippable grip projectingly formed on a side of at least one of the donor portion and the reference portion.

6. The iontophoresis patch according to claim 1, wherein the donor portion has, on a surface thereof opposite to the first contact member, a central mark indicative of the center of the first contact member as viewed in plan, and an angle mark indicative of a rotational angle of the first contact member as viewed in plan.

* * * * *